(12) United States Patent
Atkinson et al.

(10) Patent No.: US 6,717,663 B2
(45) Date of Patent: Apr. 6, 2004

(54) OPTICAL CONFIGURATION AND METHOD FOR DIFFERENTIAL REFRACTIVE INDEX MEASUREMENTS

(75) Inventors: Robert C. Atkinson, Buffalo, NY (US); Thomas E. Ryan, Batavia, NY (US); Keshav Sharma, Lancaster, NY (US); Michael J. Byrne, East Aurora, NY (US)

(73) Assignee: Reichert, Inc., Depew, NY (US)

( * ) Notice: Subject to any disclaimer, the term of this patent is extended or adjusted under 35 U.S.C. 154(b) by 0 days.

(21) Appl. No.: 10/094,213

(22) Filed: Mar. 8, 2002

(65) Prior Publication Data

US 2003/0169417 A1 Sep. 11, 2003

(51) Int. Cl.$^7$ ............................................... G01N 21/41
(52) U.S. Cl. ....................................................... 356/136
(58) Field of Search ................................. 356/128–137

(56) References Cited

U.S. PATENT DOCUMENTS

| | | | |
|---|---|---|---|
| 4,042,304 A | * 8/1977 | Martin et al. ................ 356/128 |
| 4,126,393 A | 11/1978 | Sumikama et al. ......... 356/130 |
| 4,640,616 A | 2/1987 | Michalik ..................... 356/136 |
| 4,834,104 A | * 5/1989 | Kreinick et al. ............ 600/300 |
| 4,952,055 A | 8/1990 | Wyatt ........................... 356/73 |
| 5,157,454 A | 10/1992 | Oka et al. .................... 356/130 |
| 5,305,071 A | 4/1994 | Wyatt ........................... 356/73 |
| 5,313,264 A | 5/1994 | Ivarsson et al. .............. 356/72 |
| 5,398,110 A | 3/1995 | Kitaoka ....................... 356/130 |
| 5,617,201 A | 4/1997 | K.ahre ......................... 356/135 |
| 6,127,183 A | 10/2000 | Ivarsson et al. .............. 436/34 |
| 6,128,080 A | * 10/2000 | Janik et al. .................. 356/491 |
| 6,172,746 B1 | 1/2001 | Byrne et al. ................ 356/135 |
| 6,396,576 B1 | * 5/2002 | Bleyle ........................ 356/128 |

\* cited by examiner

Primary Examiner—Hoa Q. Pham
(74) Attorney, Agent, or Firm—Hodgson Russ LLP (57) ABSTRACT

An optical configuration for differential refractive index measurements of a test sample relative to a reference sample comprises an optical path along which an illumination beam travels to simultaneously illuminate a pair of optical interfaces on opposite sides of a meridional plane corresponding to the test sample and reference sample, respectively. Partial beams leaving the optical interfaces are optically diverged to illuminate different segments of a linear scanned array aligned in the meridional plane. The difference in location of a pair of shadowlines or a pair of resonance minimums formed by the partial beams on the array provides an indication of the refractive index difference.

45 Claims, 11 Drawing Sheets

OPTICAL CONFIGURATION AND METHOD FOR DIFFERENTIAL REFRACTIVE INDEX MEASUREMENTS

BACKGROUND OF THE INVENTION

I. Field of the Invention

The present invention relates generally to optical instruments for measuring refractive index of a substance, and more particularly to an optical configuration and method for measuring a difference in refractive index between a test sample and a reference sample. The present invention is applicable to differential refractometers and surface plasmon resonance (SPR) biosensor devices.

II. Description of the Related Art

Refractometers measure the critical angle of total reflection by directing an obliquely incident non-collimated beam of light at a surface-to-surface boundary between a high refractive index prism and a sample to allow a portion of the light to be observed after interaction at the boundary. In transmitted light refractometers, light that is transmitted through the sample and prism is observed, while in reflected light refractometers, the light that is reflected due to total reflection at the surface-to-surface boundary is observed. In either case, an illuminated region is produced over a portion of a detection field of view, and the location of the shadowline between the illuminated region and an adjacent dark region in the detection field of view allows the sample refractive index to be deduced geometrically. Differential refractometers, for example that disclosed in U.S. Pat. No. 5,157,454, have been developed for measuring a difference in refractive index between a test sample and a known reference sample, whereby variable test conditions effecting the measurement result, such as sample temperature, illumination level, etc., can be "subtracted out" to yield a more accurate and precise measurement result. The prior art differential refractometers known to applicants involve moving parts which malfunction or wear out over time, and/or are restricted to the transmitted light variety so as to prevent measurement of samples having relatively high opacity.

Optical biosensor devices designed to analyze binding of analyte molecules to a binding layer by observing changes in internal reflection at a sensing interface are also part of the related prior art. More specifically, U.S. Pat. No. 5,313,264 to Ivarsson et al. describes an optical biosensor system that comprises a plurality of side-by-side sensing surfaces 39A–D illuminated by a streak of light 5 extending transversely across the sensing surfaces, and an anamorphic lens system 6 by which rays of light reflected from the respective sensing surfaces are imaged on corresponding columns of a two-dimensional array 7 of photosensitive elements. Accordingly, the signals from the photosensitive elements can be processed to determine a minimum reflectance associated with the resonance angle at each sensing surface. Although the system described in U.S. Pat. No. 5,313,264 avoids the use of moving parts, it is nevertheless optically complex and requires a two-dimensional array, factors that are accompanied by an increase in cost.

Finally, it is noted that one-dimensional (linear) arrays of photosensitive elements cells are commonly used in automatic refractometers designed to take non-differential readings with respect to a single test sample. Examples can be found in U.S. Pat. Nos. 4,640,616 (Michalik) and 6,172,746 (Byrne et al.). However, applicants are unaware of any critical angle optical device for differential refractive index measurements that operates using a linear array, despite the recognized economy offered by this type of array.

BRIEF SUMMARY OF THE INVENTION

Therefore, it is an object of the present invention to provide an optical configuration for differential refractive index measurements wherein a test sample and a reference sample are illuminated by a single illuminating beam.

It is another object of the present invention to provide an optical configuration for differential refractive index measurements that does not rely on moving parts.

It is a further object of the present invention to provide an optical configuration for differential refractive index measurements wherein detected light has been reflected rather than transmitted at an optical interface of the configuration.

It is a further object of the present invention to provide an optical configuration for critical angle differential refractive index measurements wherein light interacting at first and second optical interfaces corresponding to a test sample and a reference sample is detected by a single linear scanned array of photoelectric cells.

It is a further object of the present invention to provide an optical configuration for differential refractive index measurements in accordance with the objects stated above, and which operates based on surface plasmon resonance principles for use in a biosensor device.

An optical configuration formed in accordance with a first embodiment of the present invention comprises an optical path defining a meridional plane of the configuration. A high index prism in the optical path includes a sample surface divided by a partition residing in the meridional plane, such that a test sample and a reference sample supported by the sample surface are located on opposite sides of the meridional plane to establish a first optical interface associated with the test sample and a second optical interface associated with the reference sample. An illumination beam traveling along the optical path illuminates both optical interfaces simultaneously to provide a first partial beam defined by the refractive index of the test sample and a second partial beam defined by the refractive index of the reference sample. Optical means direct the first and second partial beams to illuminate different respective segments of a linear scanned array of photoelectric cells aligned in the meridional plane, whereby a difference in refractive index can be determined by a difference in shadowline location on the array. In the first embodiment, optical means includes a single wedge affixed to an exit surface of the prism in the path of the first partial beam to cause deflection thereof relative to the second partial beam.

In a second embodiment similar to the first embodiment, another wedge is affixed to the exit surface of the prism in the path of the second partial beam and in opposite orientation relative to the first wedge to achieve greater separation between the partial beams.

A third embodiment based on the first and second embodiments is an adaptation of the basic configuration in order to observe molecular interactions, particularly specific binding of analyte molecules to a binding layer, using the principles of surface plasmon resonance. In accordance with the third embodiment, a thin metallic film is applied to a slide placed on the sample surface or directly to the sample surface, and the test sample and reference sample are brought into contact with the metallic film to define first and second evanescent wave optical interfaces. In this embodiment, the locations of resonance minimums exhibited by the first and second partial beams are detected.

As taught in a fourth embodiment of the present invention, the optical means may include a pair of two-axis wedges arranged in opposite fashion in the paths of the first and second partial beams for both separating the partial beams along an axis of the linear scanned array and converging the partial beams toward the meridional plane to arrive at the linear scanned array. As an alternative to using two-axis wedges, a pair of single axis wedges may be used in combination with a cylinder lens or biprism between the prism and linear scanned array.

The present invention further encompasses methods for measuring a difference in refractive index between a test sample and a reference sample based on the specified optical configurations.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

An optical configuration formed in accordance with a first embodiment of the present invention will now be described with reference being made to FIGS. 1A–6 of the drawings. The optical configuration of the first embodiment is shown generally at FIGS. 1A and 1B and is designated by the reference numeral 10. Optical configuration 10 includes an illumination beam 12 traveling along an optical path OP from the beam's origin at a light source 11. Illumination beam 12 travels sequentially through a diffuser 14, a polarizer 16, a collimating lens 18, a monochromatic filter 20 closely adjacent to collimating lens 18 for transmitting a narrow bandwidth of light having a central wavelength of 589 nm, and a focusing lens 22 closely adjacent to filter 20. The convergent illumination beam is then redirected by a mirror 24 in the direction of a high refractive index prism 26.

Figures 1A, 1B:
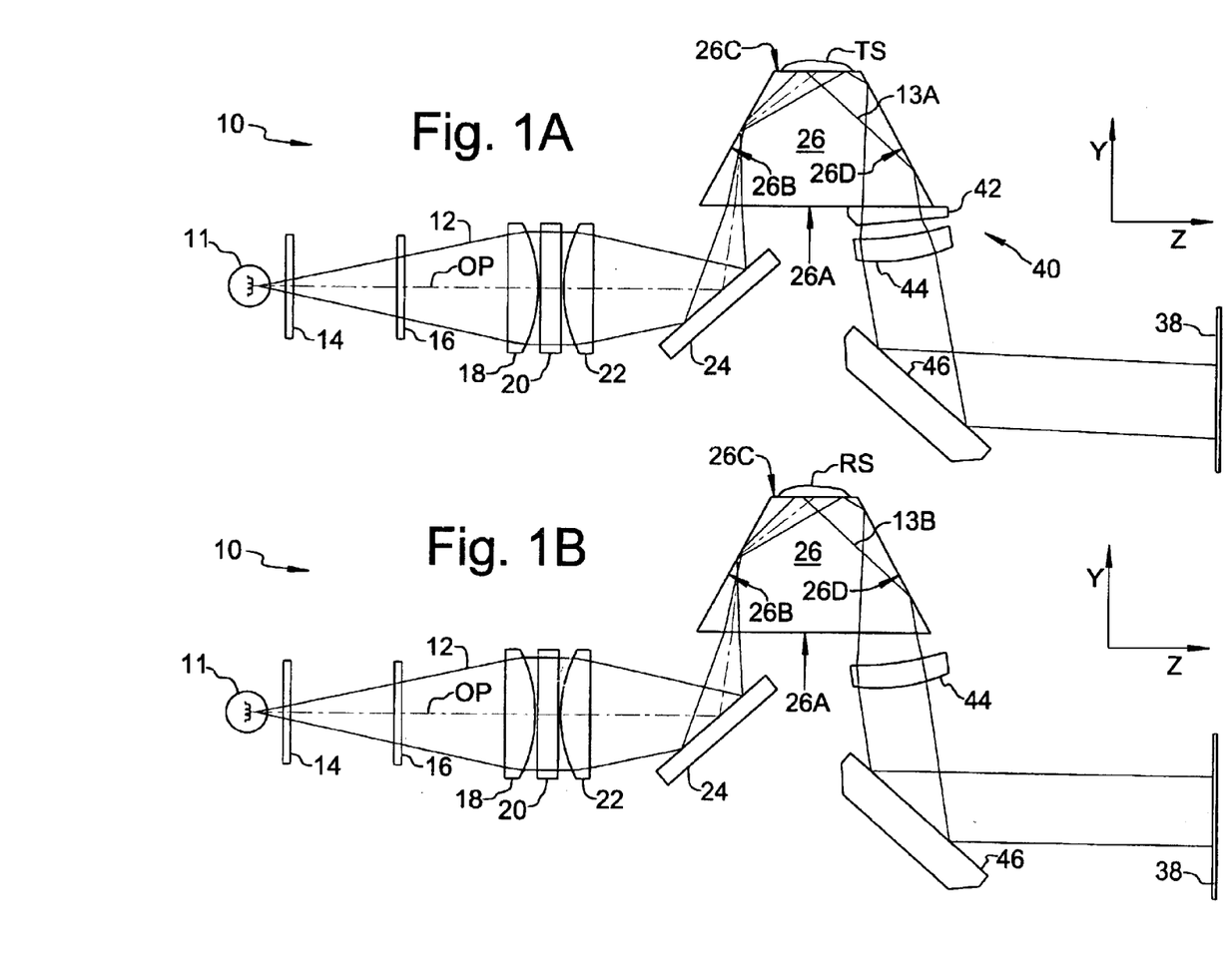
FIGS. 1A and 1B are side schematic views of an optical configuration formed in accordance with a first embodiment of the present invention for performing differential refractive index measurements based on critical angle principles, showing ray traces for a test sample (FIG. 1A) and a reference sample (FIG. 1B), respectively, wherein the test sample and reference sample are both water.
Figure 2:
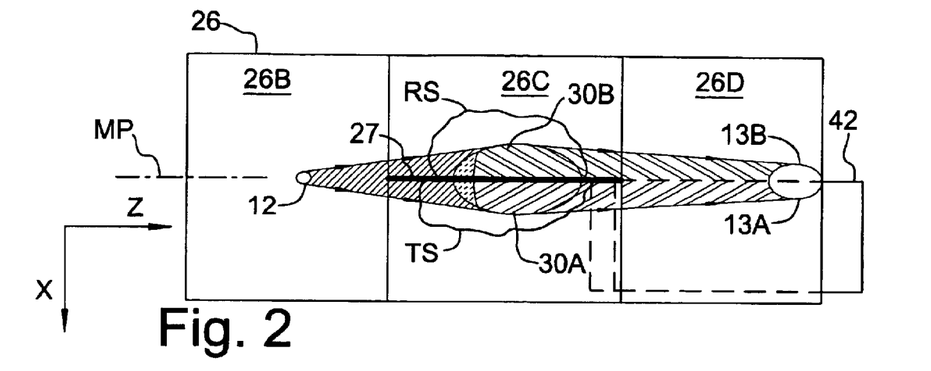
FIG. 2 is a top schematic view of an optical interface portion of the optical configuration shown in FIGS. 1A and 1B.

Prism 26, shown in top view in FIG. 2, includes a light entry/exit surface 26A, a first internally reflecting surface 26B, a sample surface 26C, and a second internally reflecting surface 26D. Sample surface 26C is divided by a partition 27 into a first area for receiving a test sample TS and a second area for receiving a reference sample RS. After being reflected by mirror 24, illumination beam 12 enters prism 26 through light entry/exit surface 26A and is reflected at first internally reflecting surface 26B such that the illumination beam is obliquely incident to sample surface 26C. In particular, illumination beam 12 approaches sample surface as a beam of non-parallel light rays, in this instance divergent light rays, that are obliquely incident to sample surface 26C at various angles of incidence within a range of angles. As can be understood most readily from FIG. 2, partition 27 is coplanar with optical path OP as the optical path approaches sample surface 26C such that the light rays making up illumination beam 12 are symmetrically apportioned between a first optical interface 30A associated with the test sample TS and a second optical interface 30B associated with the reference sample RS.

Figure 3:
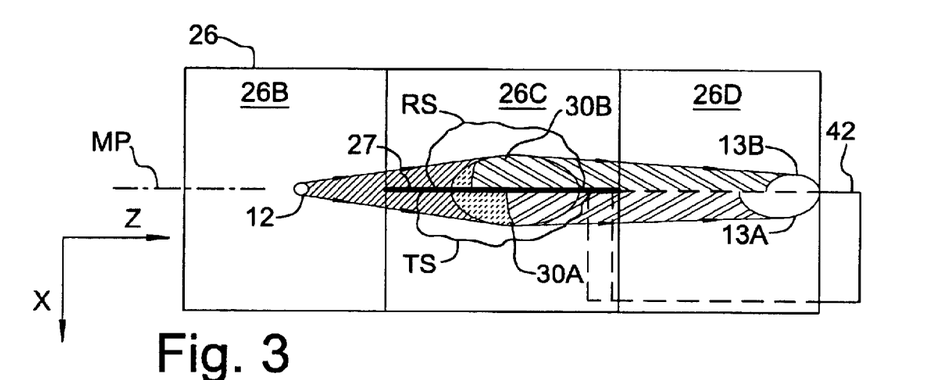
FIG. 3 is a view similar to that of FIG. 2, however the test sample is a substance having a higher refractive index than the reference sample.
Figure 4:
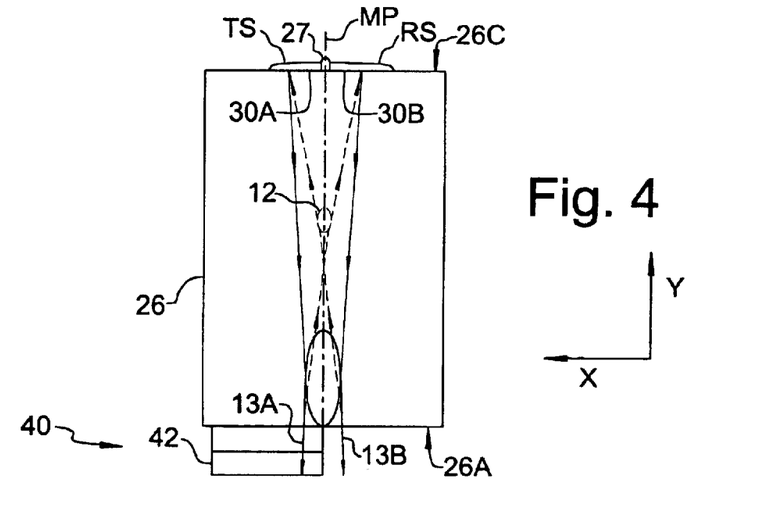
FIG. 4 is a front schematic view of the optical interface portion shown in FIG. 2.

In the present embodiment, first optical interface 30A and second optical interface 30B are critical angle optical interfaces respectively defined by the contact area of test sample TS with sample surface 26C and by the contact area of reference sample RS with sample surface 26C. These contact areas can be established by dropping the test sample TS and reference sample RS onto sample surface 26C on opposite sides of partition 27, by using a flow cell designed to bring test sample TS and reference sample RS into contact with sample surface 26C on opposite sides of partition 27, or by otherwise applying test sample TS and reference sample RS to the respective areas of sample surface 26C. The portion of illumination beam 12 reaching first optical interface 30A will interact at such interface in accordance with Snell's Law, whereby rays incident at an angle greater than or equal to the critical angle will be totally internally reflected from sample surface 26C, and rays incident at an angle less than the critical angle will be refracted and transmitted through the test sample and out of the optical system. Accordingly, the internally reflected light forms a first partial beam 13A that is defined by the index of refraction of test sample TS. A similar interaction occurs for the portion of illumination beam 12 reaching second optical interface 30B, whereby internally reflected light forms a second partial beam 13B that is defined by the index of refraction of reference sample RS. This can be better understood by comparing FIGS. 2 and 3. In FIG. 2, test sample TS and reference sample RS have the same index of refraction, whereas in FIG. 3, test sample TS and reference sample RS have different indices of refraction.

In accordance with the present invention, optical means 40 is provided for directing first partial beam 13A and second partial beam 13B to illuminate different respective segments of a linear scanned array 38 of photoelectric cells. In the first embodiment now described, optical means 40 comprises a simple "one-axis" wedge 42 preferably adhered to light entry/exit surface 26A of prism 26, such as by optical cement; a collecting lens 44 serving to compensate for optical variations in prism 26, and a mirror 46 for redirecting the light in the direction of linear scanned array 38. Wedge 42 is located such that it only receives and refracts first partial beam 13A, and does not receive and refract second partial beam 13B. By contrast, collecting lens 44 and mirror 46 receive and influence both first partial beam 13A and second partial beam 13B. As a result of the exclusive use of wedge 42 only with respect to first partial beam 13A corresponding to test sample TS, first partial beam 13A illuminates a different segment of linear scanned array 38 than does second partial beam 13B, even when the test and reference samples have the same refractive index.

Optical path OP defines a meridional plane MP in which the optical path resides. The partition 27 is aligned in meridional plane MP such that the optical configuration is divided by the meridional plane into a test sample optical system on one side of the meridional plane and a reference sample optical system on the opposite side of the meridional plane. The line of cells in linear scanned array 38 is preferably aligned to reside in meridional plane MP. It will be realized that where light source 11 approximates a true point source, neither first partial beam 13A nor second partial beam 13B will be suitably imaged on the linear scanned array because they will each arrive at the array on opposite lateral sides of the line of cells. However, the first embodiment uses a halogen bulb as light source 11, such that the lateral definition of first partial beam 13A and second partial beam 13B is not sharp enough to prevent the partial beams from illuminating the cells of linear scanned array 38. Consequently, optical means 40 does not provide any lateral redirection of first partial beam 13A or second partial beam 13B.

Figure 5:
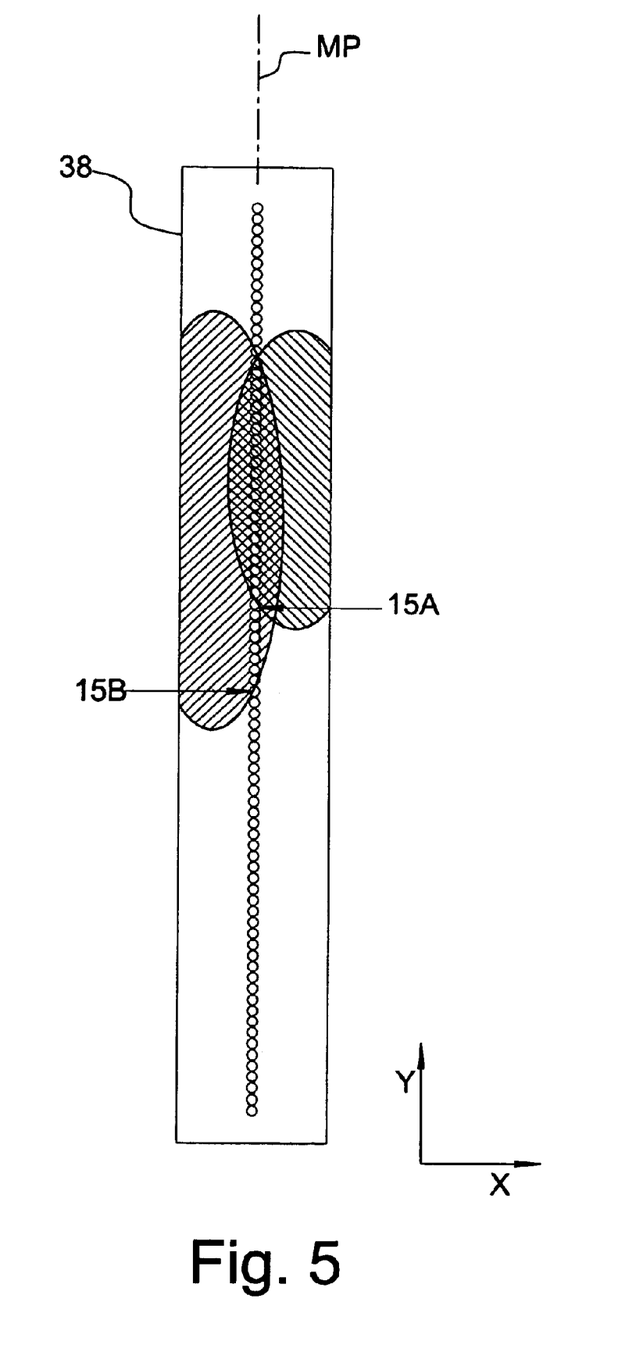
FIG. 5 is a schematic view showing an example of an illumination pattern formed on a linear scanned array in accordance with the optical configuration of the first embodiment.
Figures 6A, 6B:
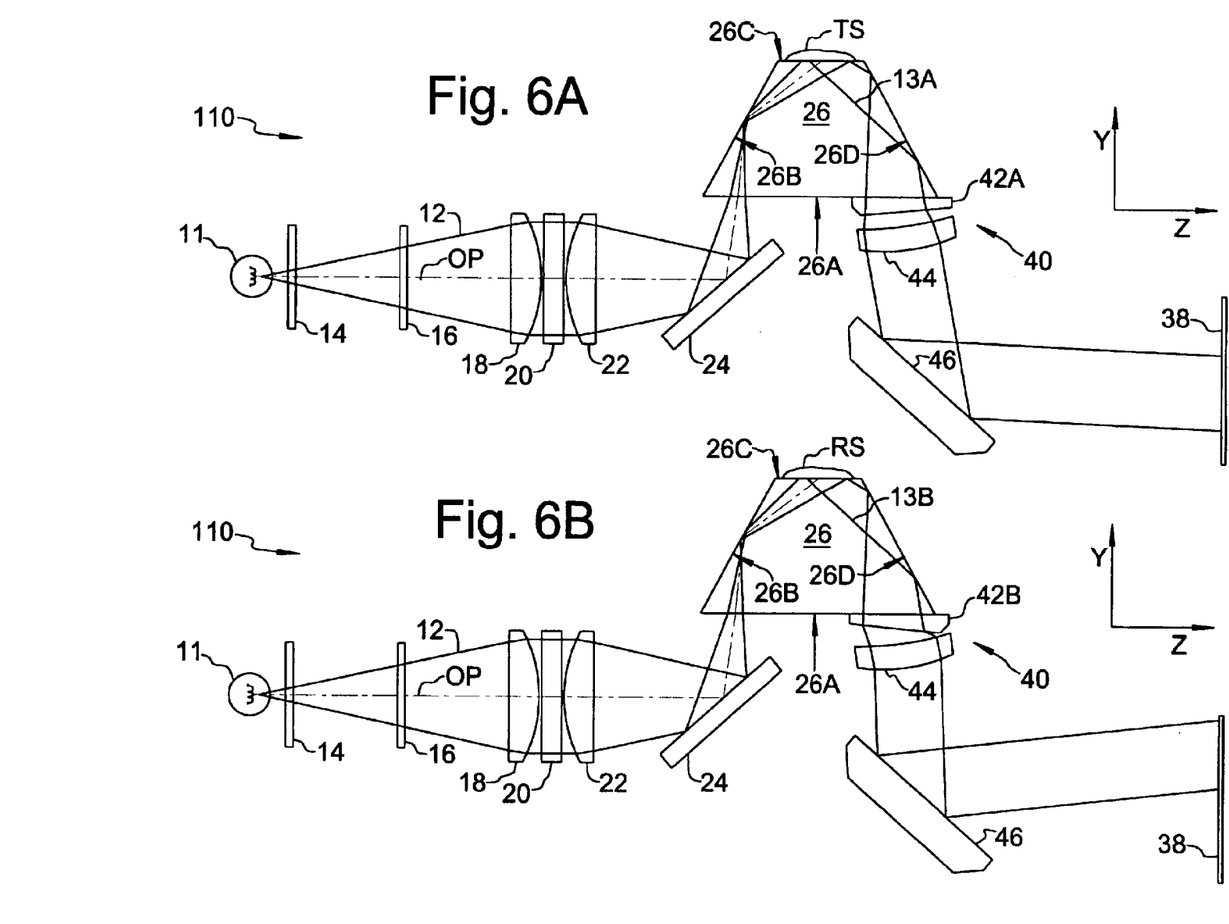
FIGS. 6A and 6B are side schematic views of an optical configuration formed in accordance with a second embodiment of the present invention similar to the first embodiment, showing ray traces for a test sample (FIG. 6A) and a reference sample (FIG. 6B), respectively, wherein the test sample and reference sample are both water.
Figure 7:
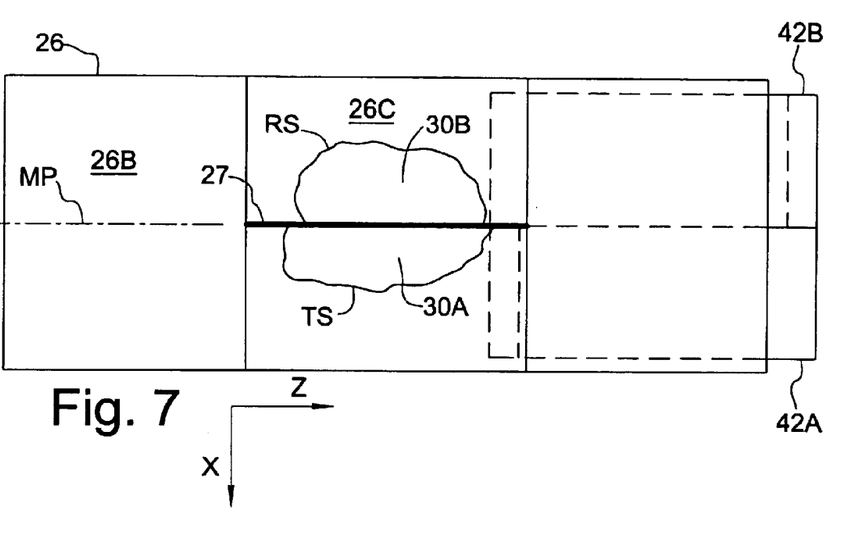
FIG. 7 is a top schematic view of an optical interface portion of the optical configuration shown in FIGS. 6A and 6B.
Figure 8:
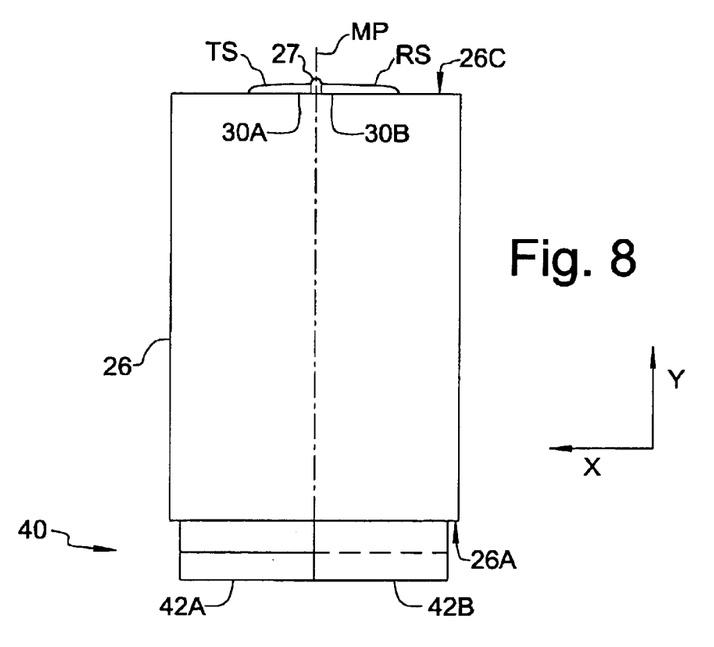
FIG. 8 is a front schematic view of the optical interface portion shown in FIG. 7.

As is well understood in the art of critical angle refractometry, and by reference to FIG. 5 herein, first partial beam 13A will exhibit a shadowline 15A at a first location on linear scanned array 38 that is indicative of the refractive index of test sample TS. In similar fashion, second partial beam 13B will exhibit a shadowline 15B at a second location on linear scanned array 38 that is indicative of the refractive index of reference sample RS. When test sample TS and reference sample RS have the same index of refraction, shadowlines 15A and 15B will be separated by a base distance determined by the influence of wedge 42 on first partial beam 13A. Once the base distance is known through calibration, it is possible to calculate a difference in refractive index between a random test sample TS and a reference sample RS by observing the distance between respective shadowlines imaged on linear scanned array 38, and determining the degree to which this observed distance deviates from the base distance. If the refractive index of the reference sample RS is known for the particular test conditions, the refractive index of the test sample TS can be calculated from the measured difference in refractive indices.

It is noted here that various algorithms are available for determining shadowline location on a linear scanned array, as taught for example by U.S. Pat. Nos. 4,640,616; 5,617,201; and 6,172,746; and by commonly-owned U.S. patent application Ser. No. 09/794,991 filed Feb. 27, 2001, each of these documents being hereby incorporated by reference in the present specification. It is further noted that the first embodiment described above was practiced by modifying an existing Leica AR600 automatic refractometer available from Leica Microsystems Inc. to include a partition 27 and a wedge 42 as described above. Purely by way of non-limiting example, an optical glass wedge having an index of refraction $N_D=1.517$, an Abbe V number V=64.5, and a wedge angle of 5° 25' was used, and partition 27 was formed by applying room temperature vulcanizing (RTV) silicon to sample surface 26C. Of course other synthetic rubber gasket materials, for example VITON® synthetic rubber composition, will provide a suitable barrier.

FIGS. 6A–8 illustrate an optical configuration formed in accordance with a second embodiment of the present invention and identified by reference numeral 110. Optical configuration 110 is similar to optical configuration 10 of the first embodiment, except that a second wedge is added to redirect second partial beam 13B in a manner opposite to first partial beam 13A to provide greater separation of the partial beams resulting in a greater base distance at linear scanned array 38. More specifically, optical means 40 includes a first wedge 42A positioned to receive first partial beam 13A and a second wedge 42B positioned to receive second partial beam 13B. First and second wedges 42A and 42B are preferably identical in material and geometry for cost savings, however second wedge 42B is rotated one-hundred eighty degrees relative to first wedge 42A. Accordingly, the thick end of first wedge 42A is closer to the center of light entry/exit surface 26A, while the thick end of second wedge 42B is closer to the outer edge of light entry/exit surface 26A.

Figure 9:
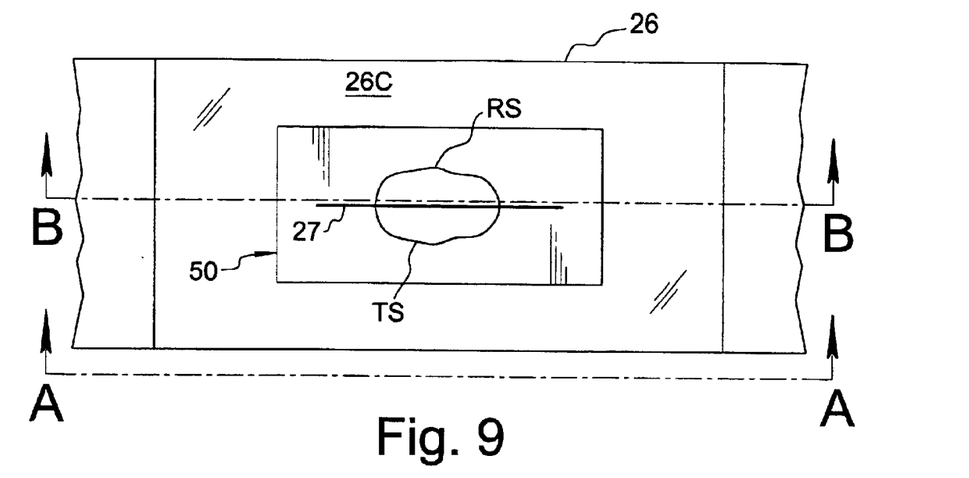
FIG. 9 is a top schematic view of an optical interface portion of an optical configuration formed in accordance with a third embodiment of the present invention for performing differential refractive index measurements based on surface plasmon resonance principles.
Figure 10A:
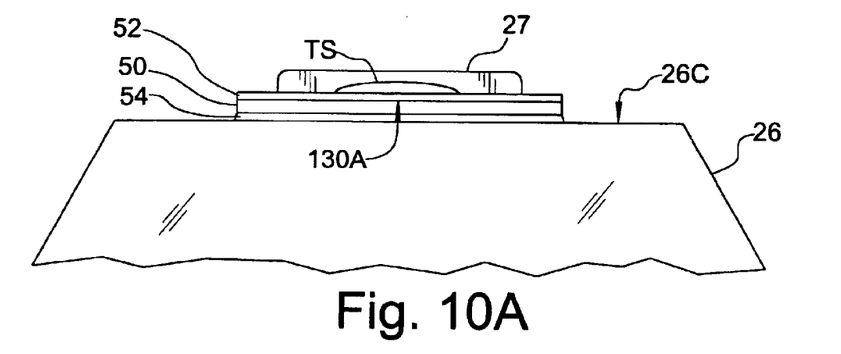
FIG. 10A is a schematic view taken generally along the line A—A in FIG. 9.
Figure 10B:
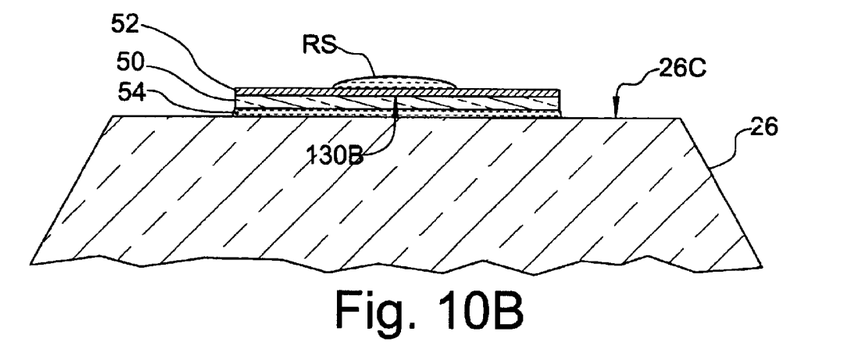
FIG. 10B is a schematic view taken generally along the line B—B in FIG. 9.
Figure 11:
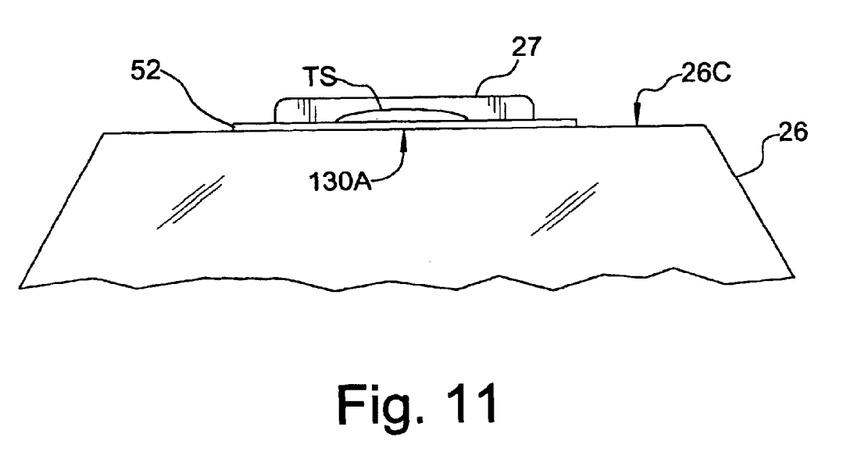
FIG. 11 is a view similar to that of FIG. 10A, showing a variation of the optical interface portion of the optical configuration of the third embodiment.

It will be understood from the above description that optical means 40 for directing first and second partial beams 13A and 13B to illuminate different respective segments of linear scanned array 38 can operate by influencing the direction of either first partial beam 13A or second partial beam 13B, or by influencing the direction of both partial beams. While optical means 40 is described as comprising a single wedge 42 or a pair of wedges 42A, 42B, it will be realized that other types of optical elements may be used to influence the direction of one or both partial beams, including but not limited to prisms, lenses, and mirrors FIGS. 9, 10A and 10B are enlarged schematic views of an optical interface portion of an optical configuration formed in accordance with a third embodiment of the present invention for performing differential refractive index measurements based on surface plasmon resonance principles. The third embodiment is similar in all respects to the first embodiment described above, except that the respective optical interfaces 130A and 130B for test sample TS and reference sample RS are evanescent wave optical interfaces rather than critical angle optical interfaces, and narrow band-pass filter 18 preferably transmits light having a central wavelength of 780 nm. A glass slide 50 is provided with a thin metallic film 52 on an upwardly facing surface thereof. In the present embodiment, metallic film 52 includes a layer of chromium approximately ten angstroms thick for adherence to the glass surface of slide 50, and a gold layer approximately fifty nanometers thick. A gasket material, such as RTV silicon, is applied to metallic film 52 to provide partition 27. Metallic film 52 is optically coupled, indirectly, to prism sample surface 26C through transparent glass slide 50 and a thin layer of transparent oil 54 provided between the underside of glass slide 50 and sample surface 26C. Of course, metallic film 52 can be optically coupled to sample surface 26C by applying the film directly to sample surface 26C, as illustrated in FIG. 11. Test sample TS and reference sample RS are contacted with metallic coating 52 on opposite sides of partition 27, such that respective first and second optical interfaces are established. As light from illumination beam 12 reaches metallic film 52 at the first optical interface, certain rays will be incident at a resonance angle determined by the refractive index of test sample TS and energy associated with such rays will be absorbed, while the remainder of the rays will be internally reflected by metallic film 52. As a result, first partial beam 13A exhibits a resonance minimum at a first location on linear scanned array 38 that is indicative of the refractive index of test sample TS. Likewise, second partial beam 13B will exhibit a resonance minimum at a second location on linear scanned array 38 that is indicative of the refractive index of reference sample RS.

Figure 12:
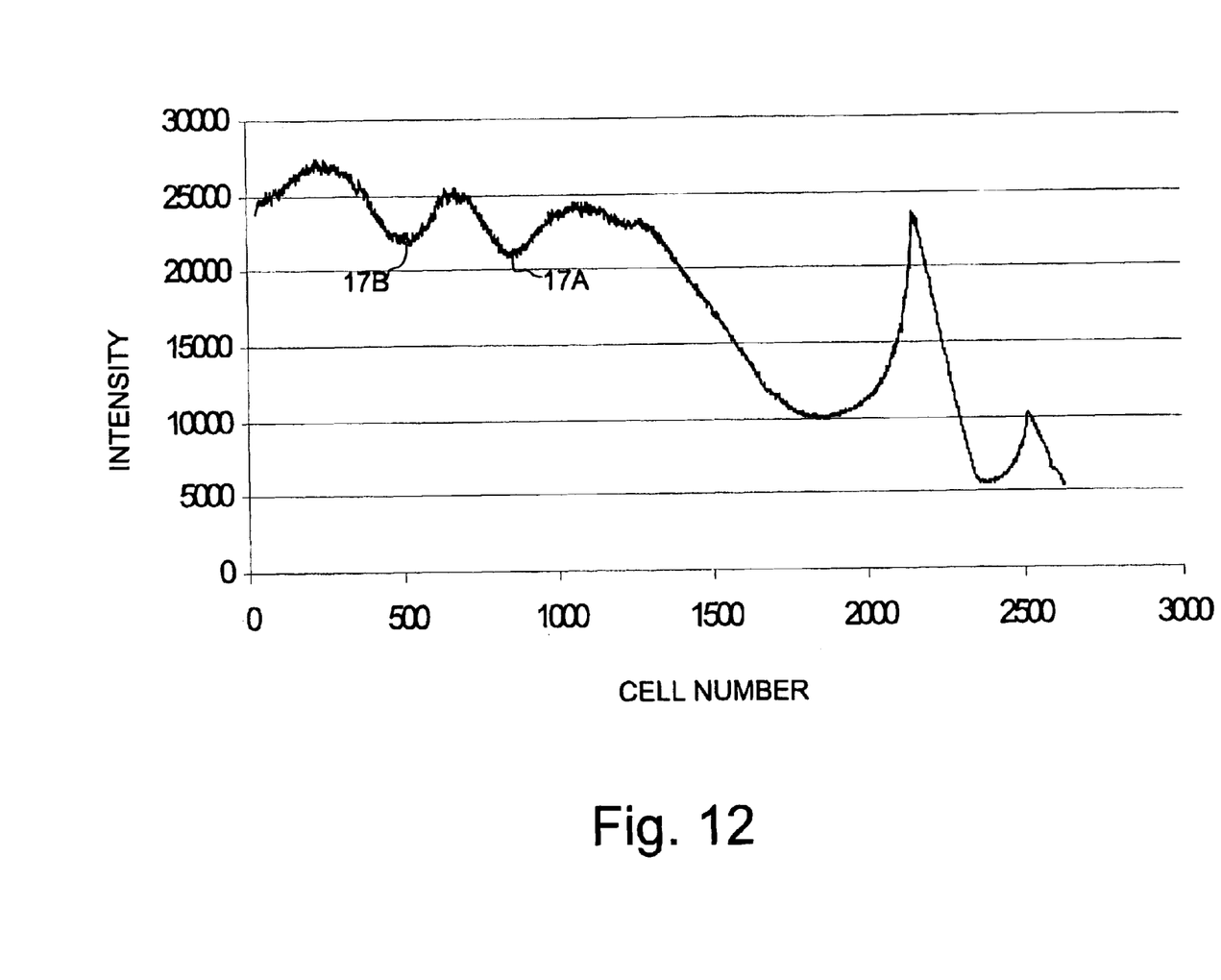
FIG. 12 is a plot of light intensity as a function of cell number based on signals from a linear scanned array in accordance with an optical configuration of the third embodiment, with water serving as both test sample and reference sample.

When test sample TS and reference sample RS have the same index of refraction, the respective resonance minimums will be separated by a base distance determined by the influence of wedge 42 on first partial beam 13A. Once the base distance is known through calibration, it is possible to calculate a difference in refractive index between a random test sample TS and a reference sample RS by observing the distance between respective resonance minimums imaged on linear scanned array 38, and determining the degree to which this observed distance deviates from the base distance. If the refractive index of the reference sample RS is known for the particular test conditions, the refractive index of the test sample TS can be calculated from the measured difference in refractive indices. The illumination curve plotted in FIG. 12 demonstrates the appearance of detectable resonance minimums 17A and 17B at first and second locations along linear scanned array 38.

The present embodiment based on evanescent wave principles finds useful application in the observation of molecular interactions, particularly in the analysis of specific binding of analyte molecules to a binding layer. Accordingly, prepared slides having a predetermined, application-specific binding layer applied to metallic film 52 can be produced for use with a variety of analytes.

FIGS. 13–18 show an optical configuration 210 formed in accordance with a fourth embodiment of the present invention. Optical configuration 210 comprises an illumination source 211 providing an illumination beam 212 that travels along an optical path OP sequentially through a diffuser 214, a collimating lens 215, a narrow band-pass filter 216, a linear polarizer 218, and a focusing lens 220. A pin-hole aperture 222 is located in the focal plane of focusing lens 220. The divergent beam 212 is then re-focused by a high refractive index glass lens 224 before entering a high refractive index prism 226 that includes a light entry surface 226A, a sample surface 226B contacted by test sample TS and reference sample RS, and a light exit surface 226C. Preferably, lens 224 is affixed with optical cement to light entry surface 226A of prism 226. The illuminating light is focused at a point within prism 226 near sample surface 226B, after which point the beam once again becomes divergent. As can be understood from FIG. 15, the divergent beam is obliquely incident to sample surface 226B, such that non-parallel light rays are obliquely incident to sample surface 226B at various angles of incidence within a range of angles.

Similar to the previous embodiments, sample surface 226B is divided by a linear partition 227 that is coplanar with the meridional plane defined by optical path OP such that the light rays making up illumination beam 212 are symmetrically apportioned between a first optical interface 230A associated with the test sample TS and a second optical interface 230B associated with the reference sample RS. The portion of illumination beam 212 that is internally reflected at optical interface 230A becomes first partial beam 213A, and the portion of illumination beam 212 that is internally reflected at optical interface 230B becomes second partial beam 213B. First and second beam portions 230A and 230B leave prism 226 through light exit surface 226C.

Figures 13, 14:
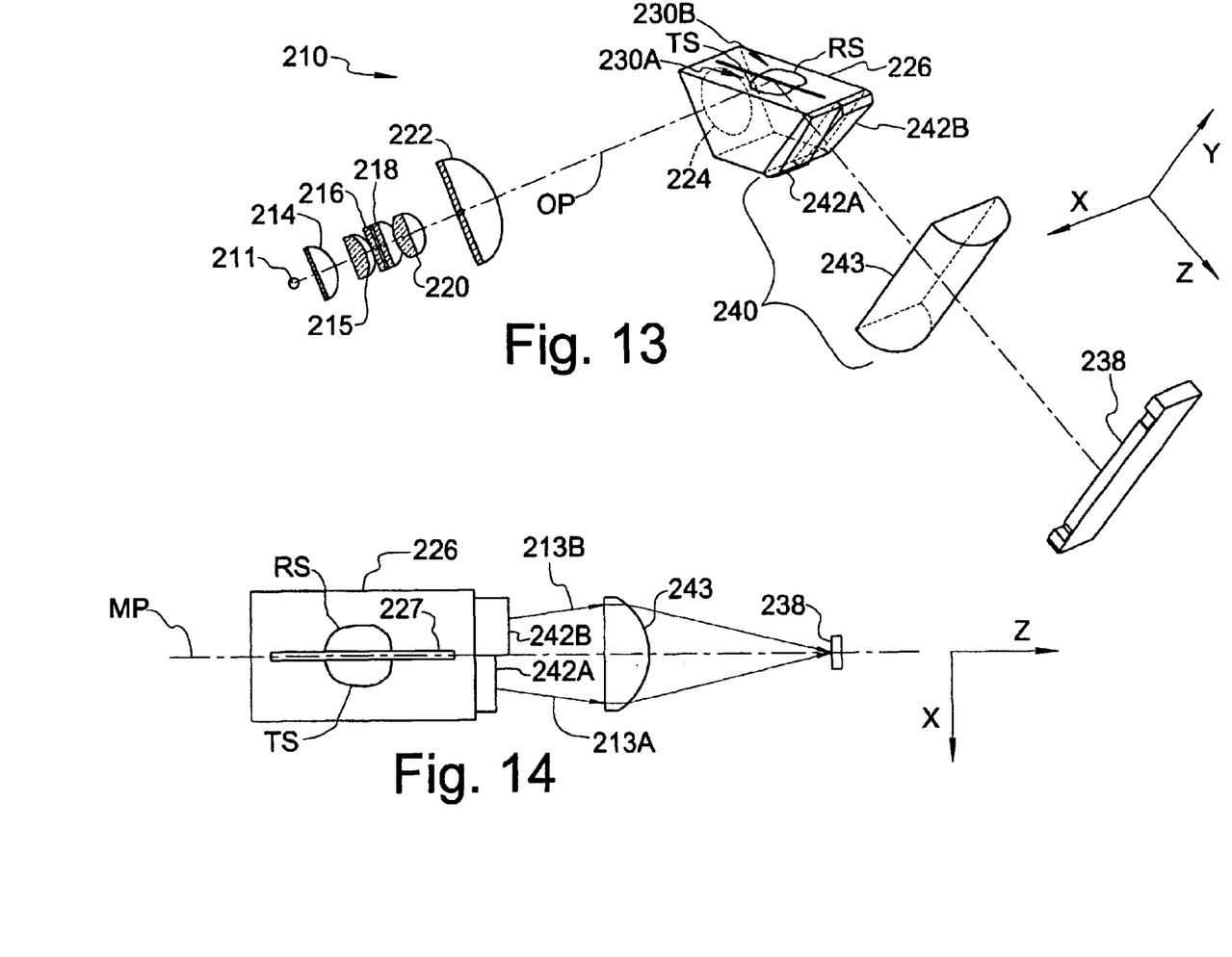
FIG. 13 is a side schematic view of an optical configuration formed in accordance with a fourth embodiment of the present invention.
FIG. 14 is a top schematic view of the optical configuration shown in FIG. 13.
Figure 15:
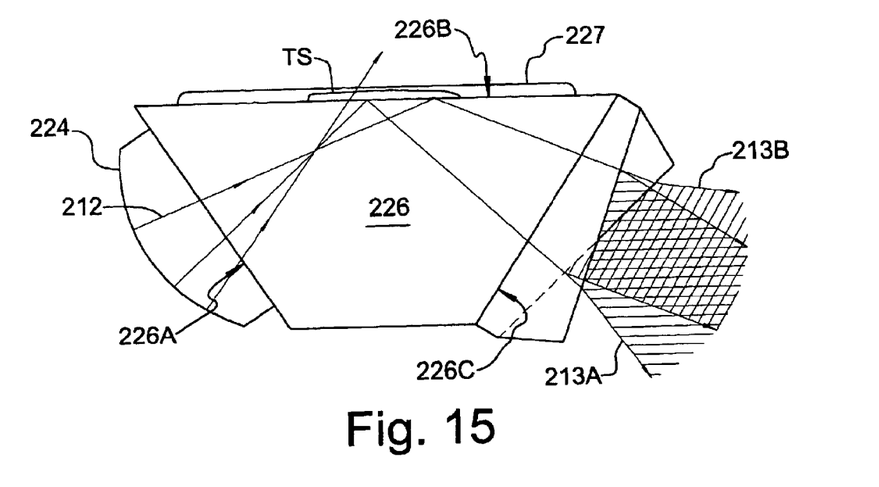
FIG. 15 is an enlarged detail view directed to optical means of the optical configuration shown in FIG. 13.
Figure 16:
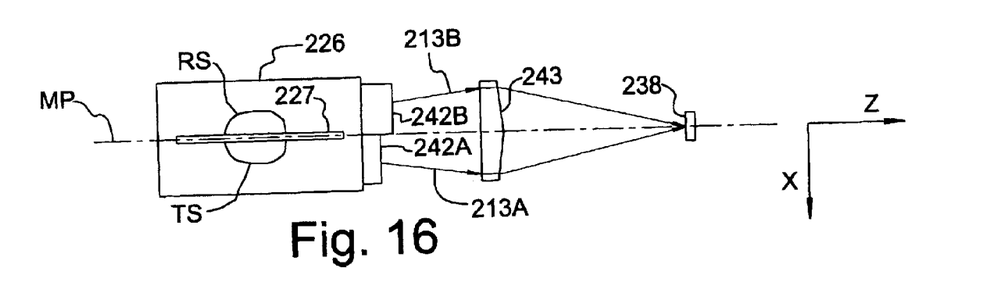
FIG. 16 is a view similar to that of FIG. 14, showing a variation of the optical configuration shown in FIGS. 13 and 14 utilizing a biprism as part of the optical means thereof.

Optical means 240 is provided for directing first partial beam 213A and second partial beam 213B to illuminate different respective segments of a linear scanned array 238 of photoelectric cells. In the present embodiment, illumination beam 212 originates from a well-defined point source, and optical means 240 functions to direct partial beams 213A and 213B in convergent X-axis directions laterally inward toward the meridional plane MP of the configuration for receipt by the cells of linear scanned array 238, and in divergent Y-axis directions such that the partial beams illuminate different segments of the array. In the embodiment of FIGS. 13–16, the function of separating the partial beams along a Y-axis (array cell line) of the system is performed by a pair of identical but oppositely arranged one-axis wedges 242A, 242B preferably affixed to light exit surface 226C using optical cement and located to receive partial beams 213A and 213B, respectively. In this respect, the present embodiment is similar to the second embodiment described above with reference to FIGS. 7A–9. FIG. 15 is an enlarged view showing the separating influence of wedges 242A and 242B on partial beams 213A and 213B. In addition to the pair of wedges 242A and 242B, optical means 240 comprises a third optical element 243 arranged after wedges 242A and 242B for receiving both partial beams and causing the partial beams to converge from opposite lateral sides of meridional plane MP toward linear scanned array 238. Third optical element 243 is preferably a cylinder lens as shown in FIGS. 13 and 14, or a biprism as shown in FIG. 16, chosen and positioned such that partial beams 213A and 213B are directed laterally inward toward meridional plane MP to illuminate the cells of linear scanned array 238.

Figure 17:
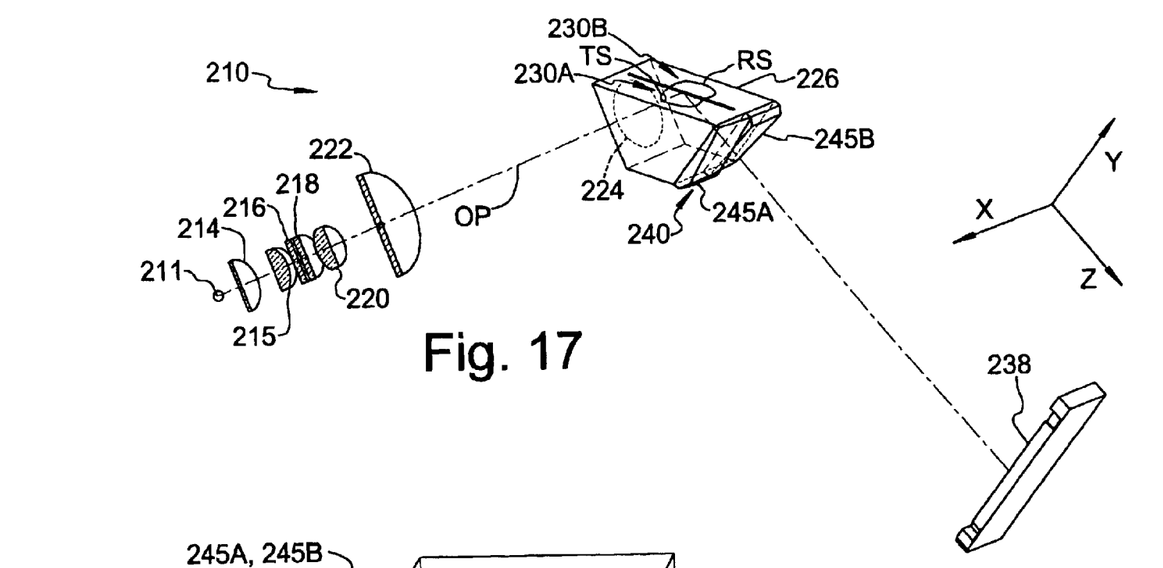
FIG. 17 is a view similar to that of FIG. 13, showing a variation of the optical configuration shown in FIGS. 13 and 14 utilizing opposite two-axis wedges as the optical means thereof.
Figure 18:
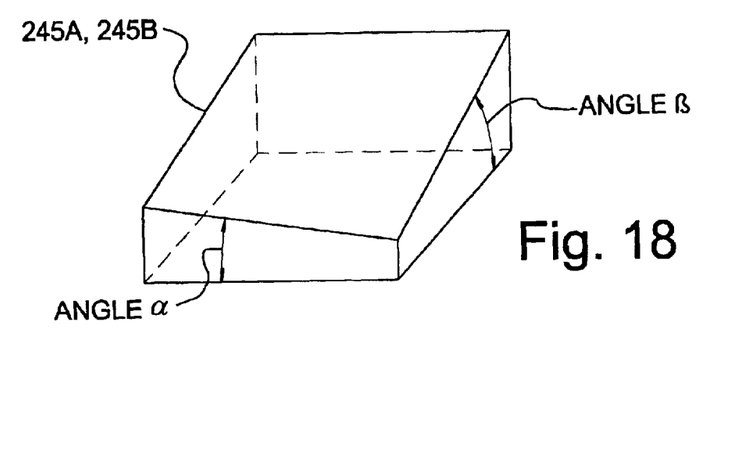
FIG. 18 is a perspective view illustrating a two-axis wedge used in the variation of FIG. 17.

In the alternative shown in FIG. 17, optical means 240 comprises a pair of oppositely arranged two-axis wedges 245A and 245B that are sloped in two orthogonal directions. A two-axis wedge is shown in greater detail in FIG. 18. Angle $\alpha$ and angle $\beta$ can be equal or nonequal angles depending on system geometry. Thus, wedges 245A and 245B diverge the partial beams along the Y-axis of the system and converge the beams along the X-axis of the system to illuminate respective segments of linear scanned array 238.

It will be recognized that the basic optical arrangements of FIGS. 13–18 can be used in connection with evanescent wave optical interfaces rather than critical angle optical interfaces by coupling a glass slide having a thin metallic film to sample surface 226B, or by directly coating sample surface 226B with a thin metallic film, in a manner analogous to the third embodiment described above.

What is claimed is:

1. An optical configuration for use in measuring a difference in refractive index between a test sample and a reference sample, said optical configuration comprising:

an optical path defining a Y-Z meridional plane of said optical configuration;

a first optical interface associated with said test sample;

a second optical interface associated with said reference sample;

said first and second optical interfaces being located on opposite sides of said Y-Z meridional plane;

an illumination beam traveling along said optical path, light from said illumination beam being incident upon said first and second optical interfaces to provide a first partial beam defined by the refractive index of said test sample and a second partial beam defined by the refractive index of said reference sample;

a linear scanned array comprising a plurality of photoelectric cells each providing an output pulse during a scan having an amplitude determined by the amount of illumination of the corresponding cell by incident light, said linear scanned array being aligned in said Y-Z meridional plane; and optical means for directing said first and second partial beams to illuminate different respective segments of said linear scanned array, said first partial beam exhibiting a feature indicative of said refractive index of said test sample at a first location on said array and said second partial beam exhibiting a feature indicative of said refractive index of said reference sample at a second location on said array;

whereby said difference in refractive index can be determined from a difference between said first and second locations on said array.

2. The optical configuration according to claim 1, wherein said first and second optical interfaces are critical angle optical interfaces, such that said first partial beam exhibits a shadowline at said first location on said array and said second partial beam exhibits a shadowline at said second location on said array.

3. The optical configuration according to claim 1, wherein said first and second optical interfaces are evanescent wave optical interfaces, such that said first partial beam exhibits a resonance minimum at said first location on said array and said second partial beam exhibits a resonance minimum at said second location on said array.

4. The optical configuration according to claim 1, wherein said first and second optical interfaces are prepared on a slide selectively movable into and out of said optical path.

5. The optical configuration according to claim 1, further comprising a prism including a light entry surface, a light exit surface, and said sample surface, said illumination beam entering said prism through said light entry surface, and said first and second partial beams exiting said prism through said light exit surface.

6. The optical configuration according to claim 5, wherein said first and second optical interfaces are formed by contacting a first area of said sample surface with said test sample and contacting a second area of said sample surface with said reference sample.

7. The optical configuration according to claim 6, further comprising a partition for dividing said sample surface of said prism along said Y-Z meridional plane to prevent mixing of said test sample and said reference sample.

8. The optical configuration according to claim 7, wherein said partition is formed of synthetic rubber.

9. The optical configuration according to claim 5, wherein said first and second optical interfaces are formed by coupling a metal film to said sample surface, said metal film having a first area contacted by said test sample and a second area contacted by said reference sample.

10. The optical configuration according to claim 9, wherein said metal film is directly coupled to said sample surface.

11. The optical configuration according to claim 9, wherein said metal film is indirectly coupled to said sample surface.

12. The optical configuration according to claim 5, wherein said optical means includes an optical element after said light exit surface of said prism for receiving and redirecting said first partial beam relative to said second partial beam.

13. The optical configuration according to claim 12, wherein said optical element is fixed to said exit surface of said prism.

14. The optical configuration according to claim 12, wherein said optical element is a wedge.

15. The optical configuration according to claim 14, wherein said wedge is a one-axis wedge.

16. The optical configuration according to claim 14, wherein said wedge is a two-axis wedge.

17. The optical configuration according to claim 5, wherein said optical means includes an optical element after said light exit surface of said prism for receiving and redirecting said second partial beam relative to said first partial beam.

18. The optical configuration according to claim 17, wherein said optical element is fixed to said exit surface of said prism.

19. The optical configuration according to claim 17, wherein said optical element is a wedge.

20. The optical configuration according to claim 19, wherein said wedge is a one-axis wedge.

21. The optical configuration according to claim 19, wherein said wedge is a two-axis wedge.

22. The optical configuration according to claim 5, wherein said optical means includes a first optical element after said light exit surface of said prism for receiving and redirecting said first partial beam relative to said second partial beam and a second optical element after said light exit surface of said prism for receiving and redirecting said second partial beam relative to said first partial beam.

23. The optical configuration according to claim 22, wherein said first optical element and said second optical element are each fixed to said exit surface of said prism.

24. The optical configuration according to claim 22, wherein said first optical element and said second optical element are each a wedge.

25. The optical configuration according to claim 24, wherein said first and second optical elements are identical one-axis wedges.

26. The optical configuration according to claim 24, wherein said first and second optical elements are identical two-axis wedges.

27. The optical configuration according to claim 22, wherein said optical means further includes a third optical element arranged after said exit surface of said prism for receiving said first and second partial beams and redirecting said first and second partial beams along converging X-axis directions.

28. The optical configuration according to claim 27, wherein said third optical element is arranged after said first and second optical elements.

29. The optical configuration according to claim 27, wherein said third optical element is a cylinder lens.

30. The optical configuration according to claim 27, wherein said third optical element is a biprism.

31. The optical configuration according to claim 5, wherein said optical means includes an optical element arranged after said exit surface of said prism for receiving said first and second partial beams and redirecting said first and second partial beams along said converging X-axis directions.

32. The optical configuration according to claim 31, wherein said optical element is a cylinder lens.

33. The optical configuration according to claim 31, wherein said optical element is a biprism.

34. The optical configuration according to claim 5, further comprising a focusing lens for focusing said illumination beam at a point within said prism, whereby said beam of light becomes a diverging cone of light, said diverging cone of light having a first symmetrical portion on a first side of said meridional plane and a second symmetrical portion on a second side of said meridional plane, said first and second symmetrical portions to be incident upon said first and second optical interfaces.

35. The optical configuration according to claim 34, wherein said focusing lens is affixed to said light entry surface of said prism.

36. The optical arrangement according to claim 34, wherein said optical means comprises a first optical element after said light exit surface of said prism for receiving and redirecting a first partial beam of said first symmetrical portion and a second optical element after said light exit surface of said prism for receiving and redirecting a second partial beam of said second symmetrical portion.

37. The optical configuration according to claim 36 wherein said first optical element and said second optical element are each fixed to said exit surface of said prism.

38. The optical configuration according to claim 36 wherein said first optical element and said second optical element are each a wedge.

39. The optical configuration according to claim 38, wherein said first and second optical elements are identical one-axis wedges.

40. The optical configuration according to claim 38, wherein said first and second optical elements are identical two-axis wedges.

41. The optical configuration according to claim 36, wherein said optical means further comprises a third optical element arranged after said exit surface of said prism for receiving said first and second partial beams and redirecting said first and second partial beams along converging X-axis directions.

42. The optical configuration according to claim 41, wherein said third optical element is a cylinder lens.

43. The optical configuration according to claim 41, wherein said third optical element is a biprism.

44. A method for measuring a difference in refractive index between a test sample and a reference sample, said method comprising the steps of:

A) providing a transparent medium having a sample surface;

B) contacting a first area of said sample surface with a test sample and a second area of said sample surface with a reference sample;

C) illuminating an interface of said transparent medium and said test sample and an interface of said transparent medium and said reference sample with a beam of light having obliquely incident divergent rays;

D) detecting a first critical angle shadowline associated with said test sample and a second critical angle shadowline associated with said reference sample on a single linear scanned array of photoelectric cells; and E) determining said difference in refractive index based on a distance between said first critical angle shadowline and said second critical angle shadowline on said linear scanned array.

45. A method for measuring a difference in refractive index between a test sample and a reference sample, said method comprising the steps of:

A) providing a transparent medium having a metal film adhered thereto;

B) contacting a first area of said metal film with a test sample and a second area of said metal film with a reference sample;

C) illuminating an interface of said transparent medium and said metal film with a beam of light having divergent rays obliquely incident to said interface, said beam of light simultaneously irradiating said interface at a first region opposite said first area and a second region opposite said second area;

D) detecting a first resonance induced flux minimum associated with said test sample and a second resonance induced flux minimum associated with said reference sample on a single linear scanned array of photoelectric cells; and E) determining said difference in refractive index based on a distance between said first resonance induced flux minimum and said second resonance induced flux minimum on said linear scanned array.

* * * * *